United States Patent
Gartside (12)

(10) Patent No.: US 6,392,113 B1
(45) Date of Patent: May 21, 2002

(54) CATALYTIC HYDROCARBON DEHYDROGENATION SYSTEM WITH PREREACTION

(75) Inventor: Robert J. Gartside, Summit, NJ (US)

(73) Assignee: ABB Lummus Global Inc., Bloomfield, NJ (US)

(*) Notice: Subject to any disclaimer, the term of this patent is extended or adjusted under 35 U.S.C. 154(b) by 0 days.

(21) Appl. No.: 09/678,567

(22) Filed: Oct. 3, 2000

(51) Int. Cl.[7] .................. C07C 5/327; C07C 5/333; C07C 5/09
(52) U.S. Cl. .................. 585/654; 585/440; 585/616
(58) Field of Search .................. 585/654, 440, 585/616

(56) References Cited

U.S. PATENT DOCUMENTS 5,510,557 A   4/1996   Gartside et al. ............ 585/654

OTHER PUBLICATIONS

"New CATOFIN™ Process Provides Higher Conversion and Selectivity"; Gartside, Robert J.; Feldman, Robert J.; Ercan, Cemal; and Dautzenberg, Frits M.; presented in San Antonio, Texas on Mar. 22–24, 1994.

*Primary Examiner*—Walter D. Griffin
*Assistant Examiner*—Tam M. Nguyen
(74) *Attorney, Agent, or Firm*—Alix, Yale & Ristas, LLP

(57) ABSTRACT

The performance of an endothermic catalytic dehydrogenation process is increased without requiring additional catalyst regeneration and reheat air flow and compression by partially prereacting the preheated hydrocarbon feed and then reheating the partially dehydrogenated effluent from the prereactor to the same hydrocarbon preheat temperature prior to the main catalytic reactor. The preferable source of the heat for reheating is the effluent air from the reheat and regeneration of the catalyst in the main reactor. This same effluent air is used to regenerate the catalyst in the prereactor as needed.

5 Claims, 4 Drawing Sheets

CATALYTIC HYDROCARBON DEHYDROGENATION SYSTEM WITH PREREACTION

BACKGROUND OF THE INVENTION

This invention relates to the catalytic dehydrogenation of paraffinic and other hydrocarbons and most particularly to an endothermic catalytic dehydrogenation process involving on-stream dehydrogenation and off-stream catalyst regeneration and heating wherein the process performance is enhanced by a predehydrogenation reaction.

The catalytic dehydrogenation of paraffins is an endothermic, equilibrium-limited reaction. The extent of conversion is limited by thermodynamics with higher temperatures favoring higher conversions. In order for the dehydrogenation reaction to occur, heat must be supplied. In one type of prior art process, the catalyst is heated by contact with a heated gas, usually air. The hydrocarbon is then passed through the hot catalyst bed which supplies the heat for the endothermic reaction and lowers the catalyst temperature. At some point in time, the catalyst becomes too cool to sustain the reaction. The reactor is then taken off-stream and the catalyst is reheated by contact with the heated gas. The heated gas contains oxygen so that the heated gas also serves the additional purpose of regenerating the catalyst by the combustion of the carbonaceous deposits on the catalyst. This combustion also imparts further heat to the catalyst. After reheating and regenerating the catalyst and before putting the reactor back on-stream, the catalyst which has become oxidized must be reduced. This is done by passing a reducing gas such as hydrogen through the catalyst bed. This also supplies additional heat by the oxidation of the reducing gas. The reactor is then ready to be put back on-stream for the dehydrogenation reaction. Even further heat can be provided by injecting and combusting a fuel gas into the reheat air. Typically, the weight ratio of reheat air to hydrocarbon required to provide the process heat is between 4 and 8. In a typical cycle, the following are the percentages of heat inputs to the catalyst from the available sources:

| Feed preheat | 6% |
| Coke combustion | 18% |
| Sensible heat of air | 28% |
| Injected fuel gas | 36% |
| Heat of reduction | 12% |

The entire plant is composed of a multiplicity of reactors operating in a cyclic manner. Some of the reactors are operating with the hydrocarbon feed, some are operating with air in the reheat/regeneration mode and some are in the catalyst reduction mode.

The required air flow is set by both the desired heat requirements and by the necessity that excessive temperatures must be avoided during the reheat cycle to prevent catalyst deactivation. If the air flow were to decrease, then the injected fuel gas combustion would raise the temperature above that deactivation level. The air is provided to the process at a pressure of approximately 25 psig to overcome pressure drop through the bed which requires substantial compression equipment and power. Furthermore, the air that leaves the reactor during the reheat cycle still contains a substantial quantity of oxygen, approximately 10–15%, since high temperatures must be avoided. This represents a significant loss in process efficiency. The loss of energy up the stack is defined by the flow and temperature of the exhaust gas. The overall efficiency of the combustion process is defined by the total fuel input minus the stack losses divided by the total fuel heat input. The most efficient process is one that fully consumes all the oxygen available thus allowing for the firing of the maximum amount of fuel fired for a given flow of air and stack losses. If it is required to limit the temperature of the combustion gases as in this case where the temperature cannot exceed about 700° C., then only a fraction of the oxygen can be utilized.

Plants are typically designed to be heat input limited. For a new plant, the cost of the air handling equipment represents a major capital cost. Once designed, a plant runs to the limit of the air handling equipment. Increasing capacity requires major capital expenditures for air handling equipment in addition to the other process equipment requirements. If additional heat could be provided for the reaction without requiring equivalent increases in air flow, the plant capacity and conversion level could be readily increased and the economics and performance of the process would see considerable benefits.

SUMMARY OF THE INVENTION

An object of the invention is to increase the performance of an endothermic catalytic dehydrogenation process without requiring additional air flow and compression. The invention involves the reaction of a preheated hydrocarbon stream in a catalytic prereactor with the partially dehydrogenated effluent from the prereactor then being reheated to the same preheat temperature prior to introduction into the main catalytic reactor. More specifically, one embodiment employs the effluent air from the main reactor being reheated and regenerated to supply heat for reheating the hydrocarbon effluent from the catalytic prereactor and also for regenerating the catalyst in the prereactor. In another embodiment, the heat for reheating the hydrocarbon effluent from the prereaction can be a separately fired heater.

DESCRIPTION OF THE PREFERRED EMBODIMENTS

Figure 1A:
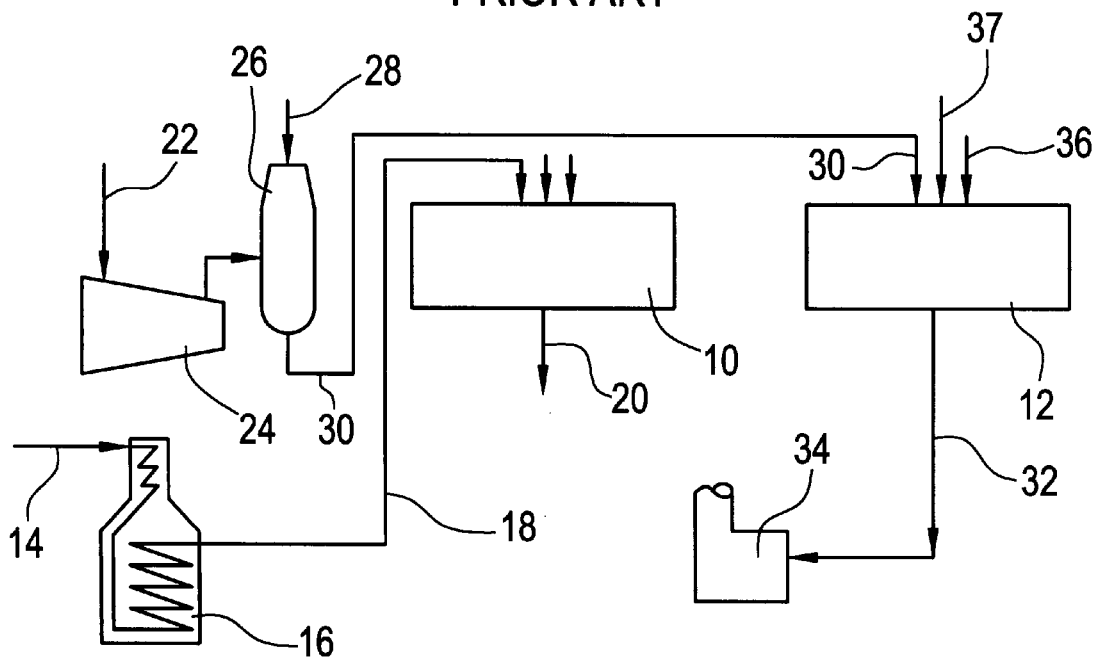
FIGS. 1A and 1B are process flow diagrams illustrating a prior art process during different stages of the process cycle.

In order to understand the nature of the present invention, the prior art process for the endothermic catalytic dehydrogenation of paraffinic hydrocarbons will be described with reference to FIGS. 1A and 1B. The system illustrated in these figures comprises two dehydrogenation reactors 10 and 12. These consist of relatively shallow catalyst beds located in long horizontal vessels. This reactor shape minimizes pressure drop by providing a large cross-sectional flow area. One of the two reactors is placed on-stream for dehydrogenation while the other reactor is off-stream for catalyst regeneration, catalyst reduction and reheating as will be explained. In FIG. 1A, the reactor is on-stream and the reactor 12 is off-stream while the reverse arrangement is shown in FIG. 1B.

The cycle begins with the preheating of the hydrocarbon feed 14 in the heater 16 and the introduction of the preheated feed 18 into the reactor 10. Typically the hydrocarbon feed is preheated to about 590° C. but it might be in the range of 400° C. to 650° C. At this point, the dehydrogenation catalyst in reactor 10 has been regenerated, reduced and heated by the previous reheat cycle. The hydrocarbon is dehydrogenated by contact with the hot catalyst producing a dehydrogenated product 20. The endothermic dehydrogenation reaction absorbs heat from and cools the catalyst bed. After a period of time, typically 7 to 15 minutes, the catalyst bed is too cool and the reaction rate is too low so the reactors are switched as discussed below.

While the reactor 10 is on-stream and dehydrogenating the hydrocarbon feed, air 22 is compressed at 24 to 25 psig or higher which heats the air. The air is further heated at 26 which involves the combustion of a fuel gas 28 which adds heat but other heating means could be used. The air is typically heated to about 625° C. but it might be in the range of 400° C. to 700° C. In FIG. 1A, the heated air 30 is fed to the off-stream reactor 12 for catalyst regeneration and reheating. The regeneration involves the combustion of coke which has been deposited on the catalyst with this combustion also adding heat to the catalyst. The catalyst is primarily reheated by the sensible heat of the air resulting from compression and the heating in combustor 26. The weight ratio of air to hydrocarbon feed required to provide the necessary process heat is typically in the range of 4 to 8. The effluent air 32 from the reactor 12, which typically contains 12 to 15% oxygen, passes to the waste heat boiler 34 for heat recovery. In some cases, it is desirable to add additional heat to the reactor directly. In these cases, additional fuel gas 37 is injected directly into the hot partially combusted air stream as it enters the reactor. The oxygen required for this combustion is provided by the oxygen in the hot air stream. The quantity of injection gas added is such that the temperature of the hot air stream is raised by 25 to 100° C. In these cases, the effluent 32 contains 9 to 14% oxygen instead of the 10 to 15% oxygen when no additional injection gas is used. After the catalyst in the reactor 12 has been regenerated and reheated, the catalyst is in an oxidized state due to the oxygen in the air and must be reduced. This is done by passing a reducing gas 36 such as hydrogen through the hot catalyst bed. The combustion of the hydrogen by the oxygen held by the oxidized catalyst provides additional heat to the catalyst bed as it reduces the catalyst to the active state.

Figure 1B:
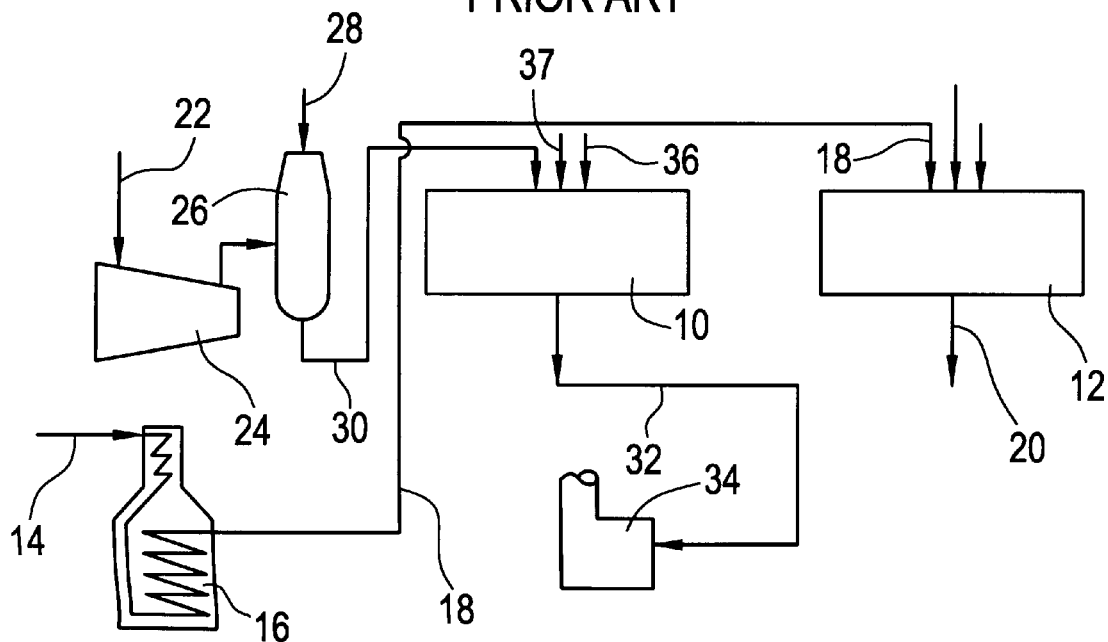

Once the catalyst in reactor 10 has cooled and the catalyst in reactor 12 has been regenerated, reduced and reheated, the process is switched to the cycle shown in FIG. 1B. In this cycle, the preheated hydrocarbon 18 is fed to the reactor 12 and the heated air 30 is fed to the reactor 10. The product 20 is now from the reactor 12 and the effluent air 32 is from the reactor 10. For a discussion of a prior art catalytic endothermic dehydrogenation process including a number of process variations, see U.S. Pat. No. 5,510,557. This patent discloses an arrangement wherein the hydrocarbon stream and the air stream are passed through the catalytic reactors in opposite directions. Such a countercurrent arrangement can also be used in the present invention.

Figure 2A:
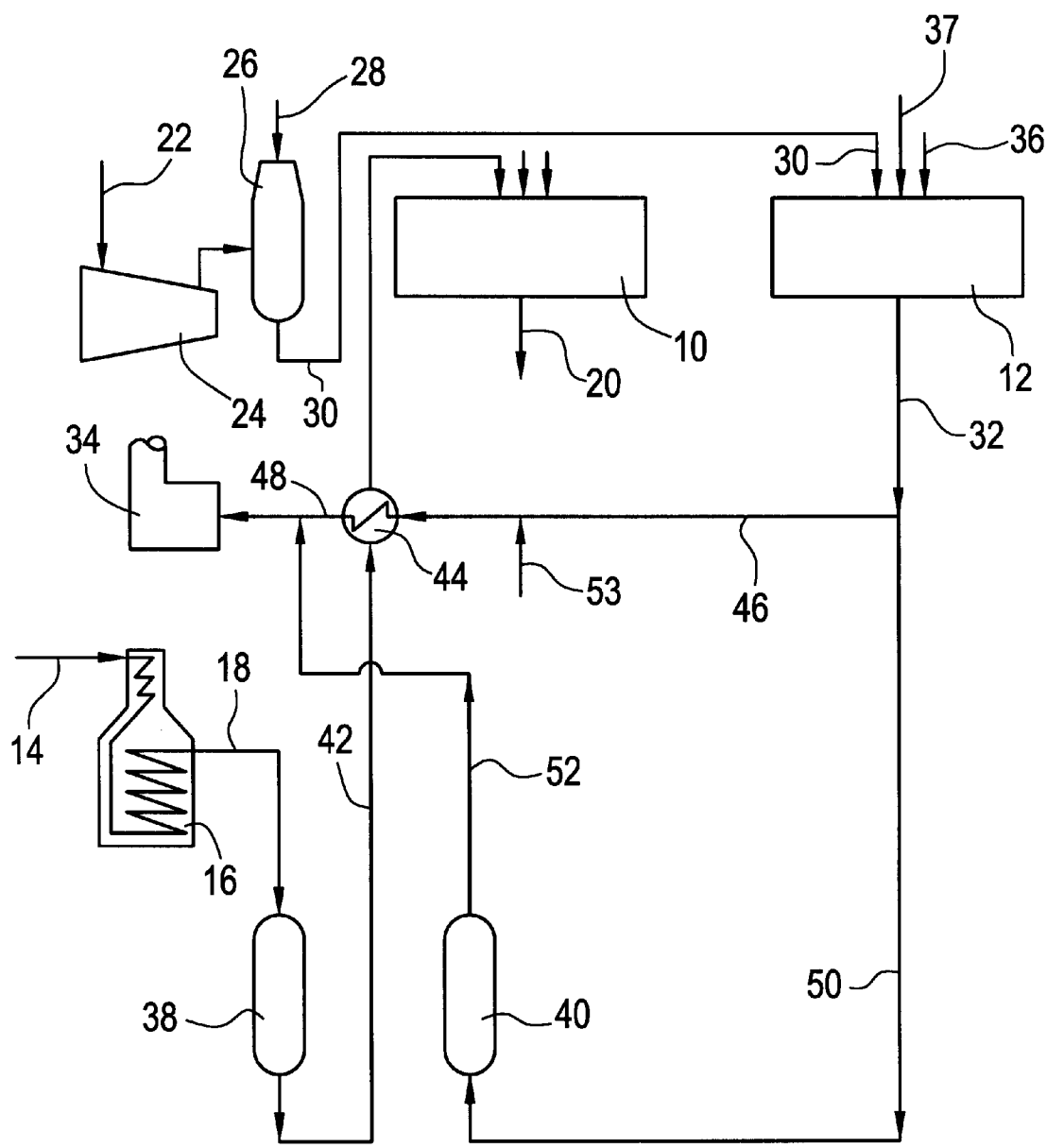
FIGS. 2A and 2B are process flow diagrams illustrating one embodiment of the present invention during the different stages of the process cycle.
Figure 2B:
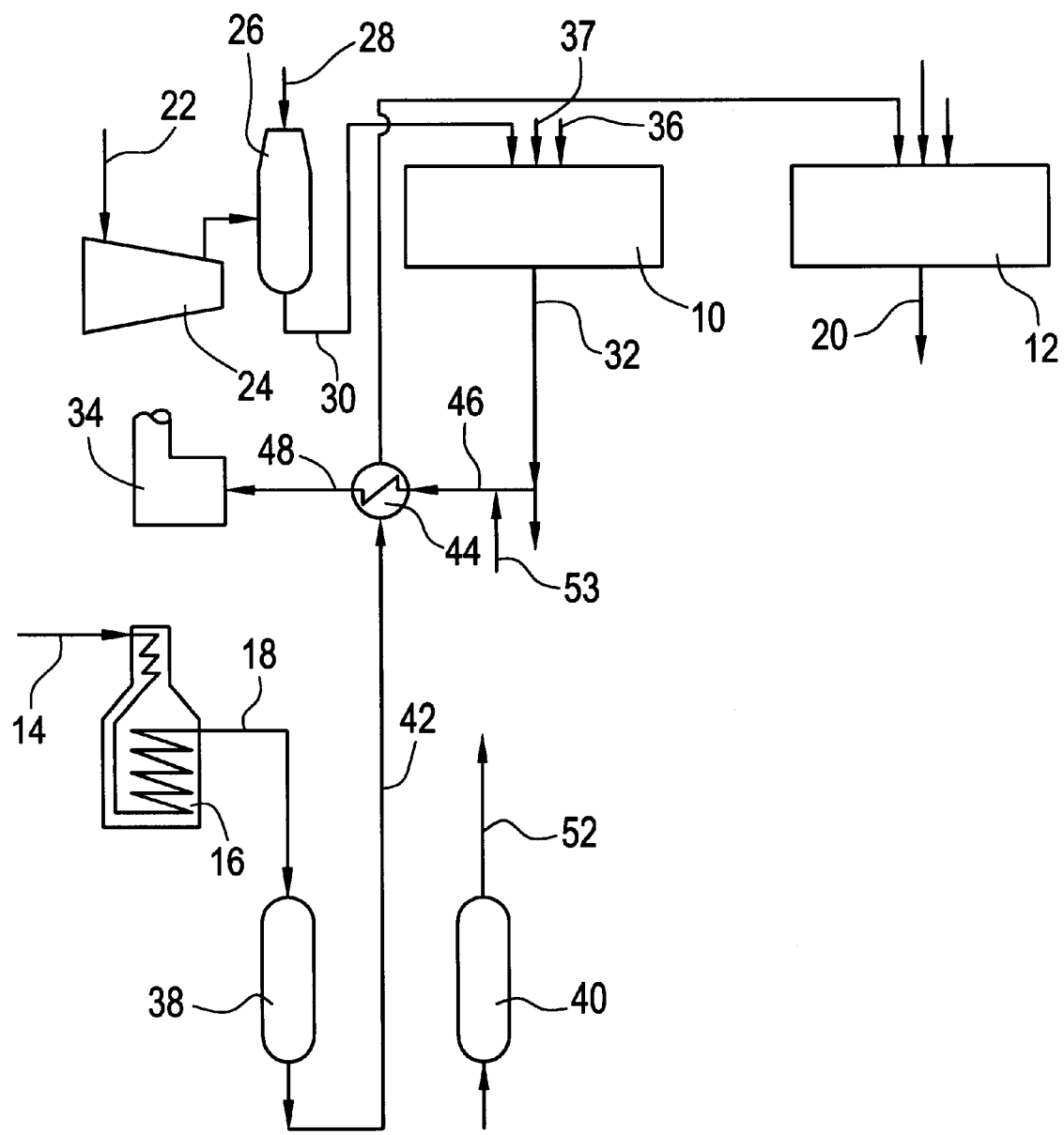

The present invention will now be described with reference first to FIGS. 2A and 2B. The system comprises the same two dehydrogenation reactors 10 and 12 as in FIGS. 1A and 1B as well as the same hydrocarbon feed 14, feed heater 16, air stream 22, compressor 24, air heating at 26 and waste heat boiler 34. The process of the invention comprises the partial dehydrogenation of the preheated hydrocarbon feed 18 in a prereactor system comprising the two prereactors 38 and 40. These prereactors 38 and 40 are preferably simple packed bed reactors containing dehydrogenation catalyst. These prereactor catalyst beds are not heated as are the main dehydrogenation catalyst beds 10 and 12. Instead, the heat required for the endothermic partial dehydrogenation in the beds 38 and 40 is provided only by the heat available in the preheated hydrocarbon stream 18. The reaction proceeds adiabatically in beds 38 and 40 only to the extent that heat is available from the feed preheat. As the temperature drops due to the endothermic heat of reaction, the reaction rate slows down. When the temperature falls too low, the reaction effectively stops. The hydrocarbon leaves the reactor at approximately 100° C. lower temperature and at a low conversion level of 10–25% depending upon feedstock. Propane, for example, will only achieve 10% conversion under these conditions while butane will achieve a higher conversion level. This reaction proceeds for a period of hours until the catalyst is deactivated due to fouling and must be regenerated. This reactor is unlike the main catalytic reactors in that it does not operate on a short cycle limited by heat content of the bed. Instead it operates for very long cycles limited by the catalyst fouling due to carbonaceous deposits from the reaction.

Since the temperature of the partially dehydrogenated hydrocarbon from the prereactor is now lower than the temperature required for the main dehydrogenation reaction, it must be reheated. In the cycle illustrated in FIG. 2A, the prereactor 38 is on-stream and the prereactor 40 is off-stream and being regenerated as may be required as described below. The partially dehydrogenated hydrocarbon 42 from the prereactor 38 is passed through the heat exchanger 44 where the partially dehydrogenated hydrocarbon is reheated back up to the desired reaction temperature, such as 590° C., by heat exchange with a portion 46 of the effluent air 32 from the reactor 12 which has a temperature in the range of 500° C. to 700° C. and typically 600° C. The exit air 48 is fed to the waste heat boiler 34. Since the hot effluent air 46 contains substantial amounts of oxygen, additional fuel 53 can be added to this stream to provide additional heat for transfer to the prereactor effluent. This will increase the temperature of the hot stream to the exchanger 44 and allow for efficient heat exchange as well as provide additional preheat to the prereactor effluent 42 before it enters the main catalytic reactor 10. Further note that while FIGS. 2A and 2B show heat exchanger 44, this could well be a fired unit with the hot air stream providing the combustion air and fuel gas provided via stream 53.

The prereactions at 38 and 40 are comparatively steady state reactions rather than cyclical as with the main reactors 10 and 12. The reaction conditions in the prereactors permit extended operation, perhaps about 24 hours, before any catalyst regeneration is required. This compares to the 7 to 15 minute cycles for the reactors 10 and 12. As shown in FIG. 2A, the prereactor 40 is being regenerated with the portion 50 of the effluent air stream 32 with the exit air 52 going to the waste heat boiler 34. FIG. 2B illustrates the next stage of the cycle with the reactor 12 being on-stream and the reactor 10 being off-stream and being reheated and regenerated. In this illustration, the prereactor 38 is still on-line while the prereactor 40 has already been regenerated and is ready to be switched with prereactor 38 when prereactor 38 needs regeneration.

The general operation of the two reactors 10 and 12 involves the heating and regeneration of a first bed of dehydrogenation catalyst with an oxygen-containing gas and then passing the reheated and partially dehydrogenated hydrocarbon through that first bed. While the hydrocarbon is passing through the prereaction dehydrogenation catalyst bed and through the first bed of dehydrogenation catalyst, the oxygen-containing gas is passed through a second bed of dehydrogenation catalyst thereby heating and regenerating that second bed. This provides a second effluent gas. The cooled partially dehydrogenated hydrocarbon is reheated by heat transfer from that second effluent gas.

Figure 3:
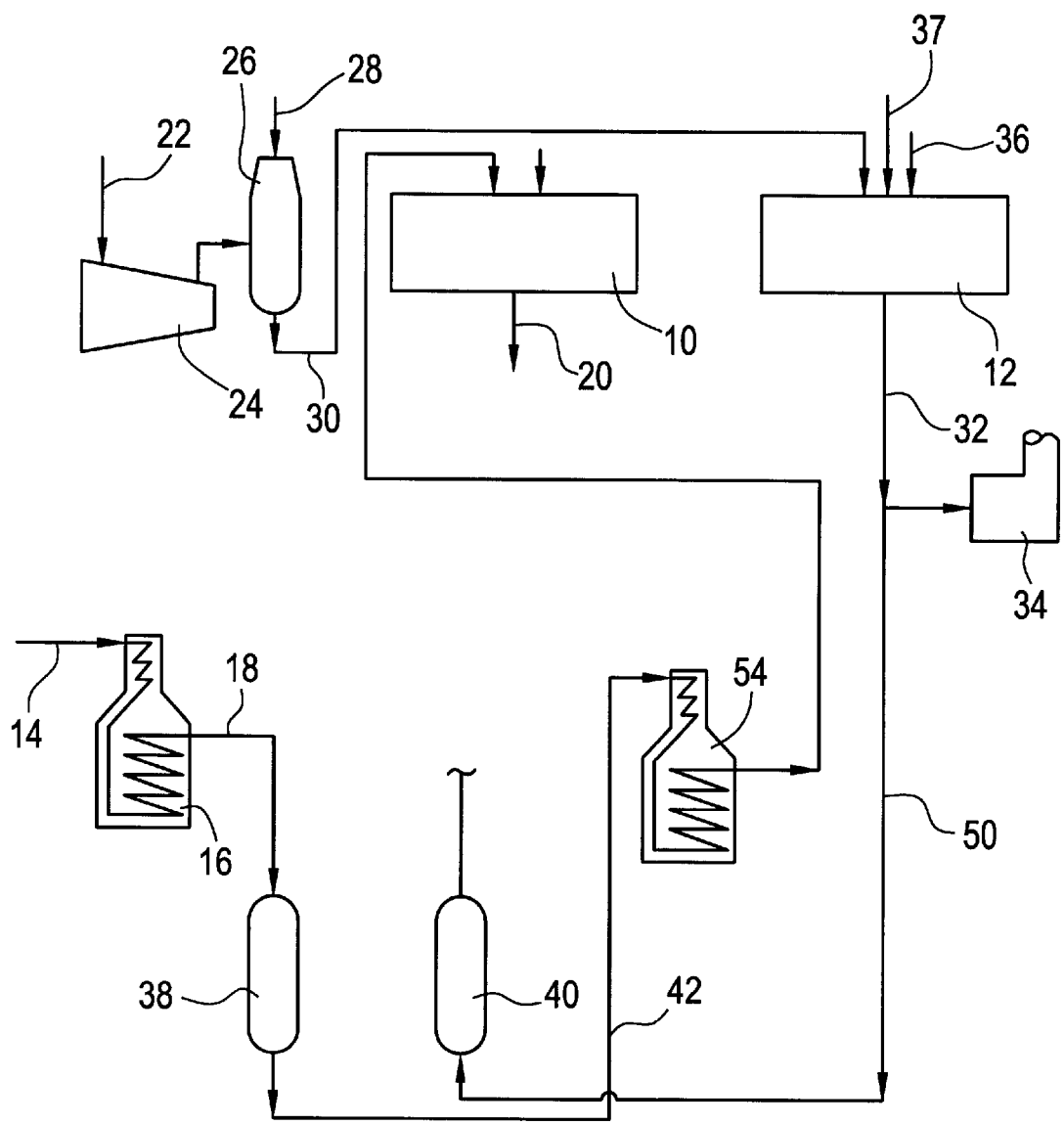
FIG. 3 is a process flow diagram illustrating another embodiment of the invention during one of its process cycles.

An alternative embodiment of the present invention is illustrated in FIG. 3. This embodiment involves the same prereactors 38 and 40 but involves an alternate way of reheating the partially dehydrogenated hydrocarbon effluent 42. As shown, the effluent 42 from the prereactor 38 is reheated in the heater unit 54. This heater unit 54 can be a fired heater, which is the type of heater illustrated, or it could be any other type of heater or heat exchanger employing a heat source other than the reheating and regeneration air stream 46 used to reheat in FIGS. 2A and 2B. However, just as with the embodiment of FIGS. 2A and 2B, the prereactors are regenerated as required with the portion 50 of the effluent air stream 32.

The principal advantage of the present invention is the ability to add heat to the reaction process without requiring additional air flow and compression. The heat added to the system without requiring air flow and compression is essentially equivalent to the heat removed via endothermic reaction in the prereactor system. The temperature of preheated feed 18 and the temperature of partially dehydrogenated feed 42 are essentially equivalent. Importantly, this heat is provided by stream 46 in FIGS. 2A and 2B thus increasing the efficiency of the entire process or by a fired heater in FIG. 3 where heat is provided also at a high efficiency of about 90% which is typical for a fired heater. This higher heat efficiency and resulting lower cost can be exploited in two ways in the overall process. The capacity of the process can be increased per unit of air flow with the capacity increase being proportional to the added heat recovery. Alternately, at the same feed rate, the conversion may be increased, within the limits of equilibrium approach of the catalyst, without an increase in the outlet temperature of the main reactors.

The following table illustrates the present invention with the prereactors to the prior art process using the same air flow and temperature and the same feed preheat temperature and feed composition:

|  | Prior Art Kg./Hr. | Invention Kg./Hr. |
| --- | --- | --- |
| Feed | 37,630 | 51,167 |
| Propylene in feed | 489 | 665 |
| Propylene in prereactor effluent |  | 4,697 |
| Propylene in final product | 15,815 | 20,868 |
| Conversion % | 49.17 | 47.12 |
| Selectivity % | 85.83 | 87.78 |

It can be seen that the invention permits an increase in the feed rate by 36% with the quantity of propylene in the product increased by 32% without any increase in the air flow and compression requirements.

What is claimed is:

1. A catalytic endothermic process for dehydrogenating hydrocarbons comprising the steps of:

a. heating an oxygen-containing gas;

b. passing said heated oxygen-containing gas through a first bed of dehydrogenation catalyst to both provide heat to said dehydrogenation catalyst for the endothermic dehydrogenation and to regenerate said catalyst by oxidizing carbonaceous deposits and thereby providing a first effluent gas;

c. preheating said hydrocarbon to a desired reaction temperature;

d. passing said preheated hydrocarbon through an unheated prereactor dehydrogenation catalyst bed wherein the exothermic heat of the dehydrogenation reaction therein is provided by said preheated hydrocarbon and said hydrocarbon is partially dehydrogenated and cooled below said desired reaction temperature;

e. reheating said cooled partially dehydrogenated hydrocarbon to said desired reaction temperature;

f. passing said reheated partially dehydrogenated hydrocarbon through said heated and regenerated first bed of dehydrogenation catalyst whereby said hydrocarbon is further dehydrogenated and said first bed of dehydrogenation catalyst is cooled.

2. A process as recited in claim 1 and further comprising the step of passing said heated oxygen-containing gas through a second bed of dehydrogenation catalyst after said first bed of dehydrogenation catalyst has been heated and regenerated and while said hydrocarbon is passing through said prereaction dehydrogenation catalyst bed and said first bed of dehydrogenation catalyst and thereby heating and regenerating said second bed of dehydrogenation catalyst and providing a second effluent gas and reheating said cooled partially dehydrogenated hydrocarbon by heat transfer from said second effluent gas.

3. A process as recited in claim 2 and further including the step of injecting a fuel gas into said second effluent gas and thereby further heating said second effluent gas.

4. A process as recited in claim 2 and further comprising the step of regenerating said prereactor dehydrogenation catalyst with a portion of said second effluent gas.

5. A process as recited in claim 1 wherein said step of regenerating said catalyst further includes the subsequent step of contacting said catalyst with a reducing gas.

\* \* \* \* \*